United States Patent
Ragauskas et al.

[11] Patent Number: 5,951,477
[45] Date of Patent: Sep. 14, 1999

[54] METHOD AND APPARATUS FOR DETERMINING THE PRESSURE INSIDE THE BRAIN

[75] Inventors: Arminas Ragauskas; Gediminas Daubaris; Algis Dziugys, all of Kaunas, Lithuania

[73] Assignee: UAB Vittamed, Bethel, Conn.

[21] Appl. No.: 08/927,613

[22] Filed: Sep. 11, 1997

[51] Int. Cl.[6] ...................................................... A61B 8/00
[52] U.S. Cl. ............................................................. 600/438
[58] Field of Search .................................... 600/437, 438, 600/531, 439, 453

[56] References Cited

U.S. PATENT DOCUMENTS

| | | |
|---|---|---|
| 4,204,547 | 5/1980 | Allocca . |
| 4,907,595 | 3/1990 | Strauss . |
| 4,930,513 | 6/1990 | Mayo et al. . |
| 4,984,567 | 1/1991 | Kageyama et al. . |
| 5,016,641 | 5/1991 | Schwartz . |
| 5,040,540 | 8/1991 | Sackner . |
| 5,117,835 | 6/1992 | Mick . |

*Primary Examiner*—Marvin M. Lateef
*Assistant Examiner*—Maulin Patel
*Attorney, Agent, or Firm*—St. Onge Steward Johnston & Reens LLC

[57] ABSTRACT

An apparatus for measuring the intracranial pressure in a non-invasive manner is described by using an ultrasonic Doppler device which detects the velocities of the blood flow inside the optic artery for both intracranial and extracranium optic artery portions. The eye in which the blood flow is monitored is subjected to a small pressure, sufficient to equalize the blood flow measurements of the internal and external portions of the optic artery. The pressure at which such equalization occurs is found to be an acceptable indication of the intracranial pressure. Various devices are illustrated and used to enable either an automatic or manual intracranial pressure measurement.

12 Claims, 5 Drawing Sheets

METHOD AND APPARATUS FOR DETERMINING THE PRESSURE INSIDE THE BRAIN

FIELD OF THE INVENTION

This invention generally relates to a method and apparatus for ultrasonically determining the intracranial pressure and more specifically relates to a method and apparatus for determining the intracranial pressure using ultrasonic measurements of the velocity of blood flow through an optic artery.

BACKGROUND OF THE INVENTION

In U.S. Pat. No. 4,907,595 an apparatus for determining the pressure and flow inside the optic artery is described. The apparatus uses a rigid chamber that can be sealingly affixed over a person's eye so that it can be pressurized to apply an external pressure against the eyeball. An ultrasonic transducer is also mounted to the chamber and oriented to inject ultrasonic pulses for a Doppler type measurement of the flow inside the optic artery. The apparatus operates by enabling an operator to increase the pressure to such a level that the blood flow through the optic artery ceases. The pressure at which this occurs is then an indication of the pressure inside the optic artery. Typically the pressure at which this event occurs is in the range of about 170 mm Hg.

A problem associated with an apparatus as described in the '595 patent is that the pressure necessary to obtain the desired measurement is so high that it exceeds generally maximum recommended pressures by a significant amount. When such device is then used for an extended time, tissue damage can arise and may result in an increase in the intracranial pressure, $P_{IC}$, to unacceptable levels.

Another ultrasonic device for determining changes in intracranial pressure in a patient's skull is described in U.S. Pat. No. 5,117,835 by placing a pair of ultrasonic transducers against the skull and storing the received signals. U.S Pat. No. 4,984,567 describes an apparatus for measuring the intracranium pressure with an ultrasonic transducer by analyzing the acoustic reflections caused by ultrasonic pulses. Other patents related to ultrasonic measuring of either intracranial pressure or other physiological features are U.S. Pat. Nos. 4,204,547; 4,930,513; 5,0116,641 and 5,040,540.

None of these prior art teachings provide a clear and non-equivocal indication of the intracranial pressure. The measurements tend to be obscured by noise arising from uncertainties in the measurements. There is, therefore, a need to be able to derive a measurement of the intracranial pressure of a person in a safe and a non-invasive manner that can be implemented with reasonable reliability.

SUMMARY OF THE INVENTION

With an apparatus in accordance with the invention one can derive an indication of the pressure inside a skull in a non-invasive manner using an ultrasonic Doppler measuring technique that is applied to the eye of a person in a safe manner.

This is achieved in accordance with one technique in accordance with the invention, by pressurizing a chamber which is in sealing engagement with a perimeter around an eye, and by using an ultrasonic Doppler measuring device, which is mounted to the chamber, to measure the internal and external blood velocities of intracranial and external cranium portions of the optic artery. Signals representative of these velocity measurements, $V_I$ and $V_E$, are then compared and their difference, $\Delta V$, used to control the pressure in the chamber. When the pressure in the chamber causes $\Delta V$ to approach a desired minimum value, that pressure becomes an indication of the intracranial pressure.

With an apparatus and technique in accordance with the invention a significantly lower pressure is applied to the eye than in the case of the above described '595 patent. The pressures typically are in the range of about 25 mm Hg, which is within a generally acceptable pressure level to avoid tissue damage and pain.

The technique of the invention can be implemented in a variety of different manners, such as with a manual increase and control over the pressure to be applied to the chamber while monitoring the internal and external velocity signals determined with the ultrasonic Doppler device. When these velocity measurements appear substantially the same the pressure at which this occurs is then used to determine the intracranial pressure.

Alternatively, by using the ultrasonic Doppler velocity measuring technique of this invention, the optic artery velocity difference measurement, $\Delta V$, can be used to directly control the pressure in the chamber by applying the signal to a pump. A pressure signal indicative of the pressure in the chamber can be used to store a signal in a suitable memory and for a display to indicate the intracranial pressure.

A still further aspect of the invention enables a measurement of the pulsatility or dynamic characteristics of a portion inside the cranium and done with an apparatus as described in U.S. Pat. No. 5,388,583 to be converted into an absolute dynamic pressure measurement.

It is, therefore, an object of the invention to provide an apparatus for determining the intracranial pressure using a non-invasive ultrasonic technique. It is a further object of the invention to obtain a measurement of the intracranial pressure of patient in a safe and dependable manner.

These and other advantages and objects of the invention can be understood from the following description of several embodiments in conjunction with the drawings.

DETAILED DESCRIPTION OF DRAWINGS

Figure 1:
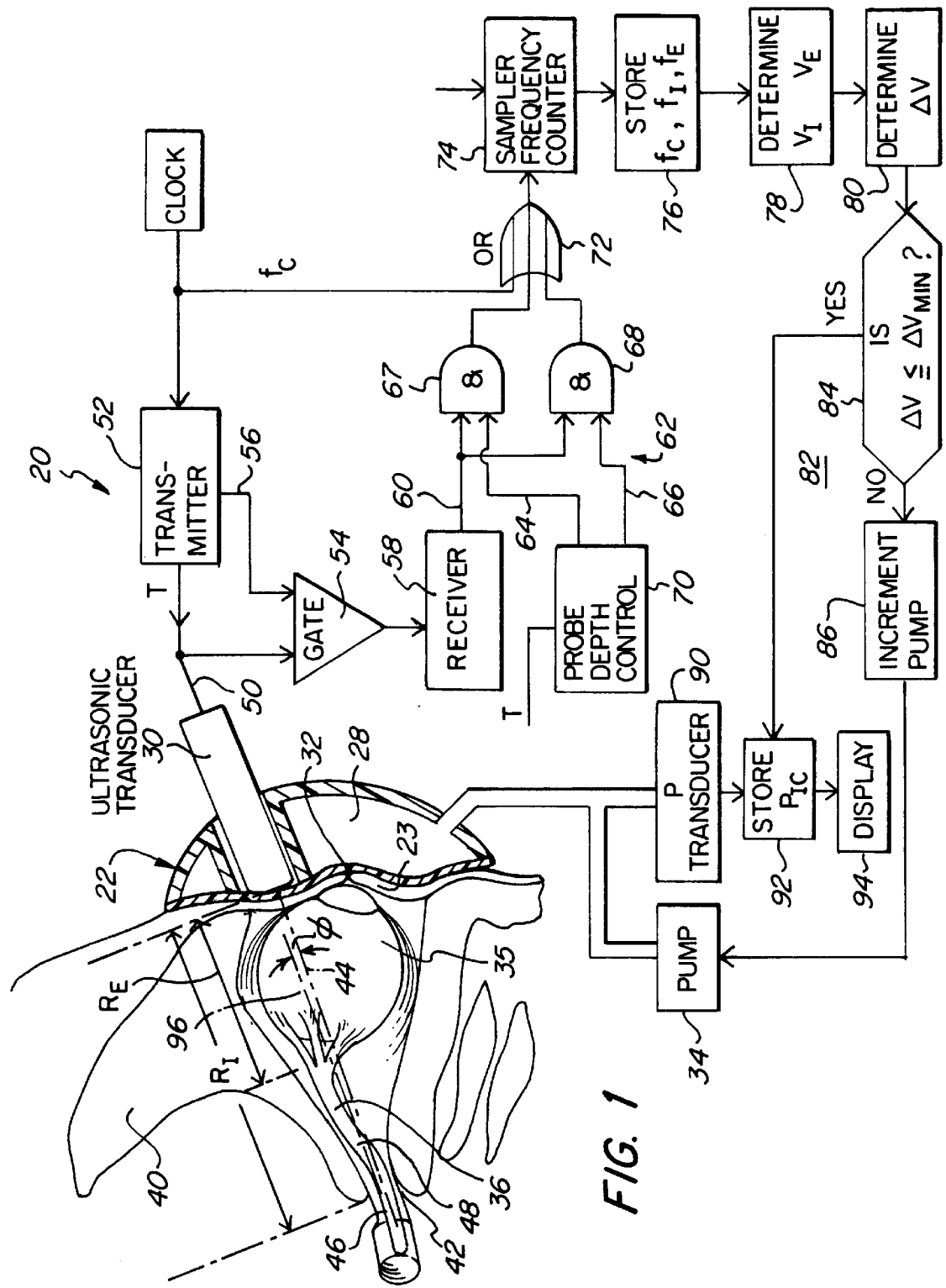
FIG. 1 is a schematic and block diagram view of an apparatus in accordance with the invention.

I have found that with an apparatus in accordance with the invention the internal pressure inside a person's head can be determined from an observation of the blood velocities inside the optic artery. This involves an ultrasonic apparatus and a device, which can apply a slight pressure to the eye, to make the internal and external blood flows in the optic artery leading to the eye the same. This type of measurement is made possible as can be demonstrated with the following analysis.

Evaluation of the Reynolds factor in the optic artery is:

$$Re = \frac{\rho V_E D_E}{\mu} = \frac{1050 \cdot 0.240 \cdot 0.001}{0.004} = 63 \tag{1}$$

Since Re<<2000 that means that the flow is laminar.

The mean value of the flow velocity within the optic artery, OA, does not depend on the distance from the intracranial middle cerebral artery but depends upon the area of the cross-section of the OA and the blood flow therein.

The influence of the pulsatility of the blood flow affects the profile of flow. The period T of blood pulsation is equal to period of the pulsation by the heart (approximately one second). The non-dimensional frequency W is equal to:

$$w = \frac{\pi \cdot D_I^2}{16 \cdot T \cdot v} \approx 0.05 \ll 1, \tag{2}$$

where $D_I$ is the internal diameter of the optic artery, OA, and the profile of blood velocity in OA is parabolic:

$$V(r) = \frac{V_E}{2}\left(1 - \frac{4r^2}{D_E^2}\right) = \frac{V_I}{2}\left(1 - \frac{4r^2}{D_I^2}\right) \tag{3}$$

where $D_E$ is the diameter of the external part of the OA, $V_E$ is the velocity of the blood flow external part of the OA, $V_I$ is the velocity off the blood flow inside the OA.

The flow F is directly proportional to mean value of the blood velocities $V_E$ and $V_I$:

$$F = \frac{4V_E}{\pi D_E^2} = \frac{4V_I}{\pi D_I^2} \tag{4}$$

It follows from equation (4) that if $V_E=V_I$, then $D_E=D_I$.

4. If the middle cerebral artery pressure is equal to $P_{MCA}$ and the pressure inside the external part of OA is equal to $P_{OAE}$ (FIG. 1) then the gradient $\Delta_P$ of pressure between two points of flow velocity measurement (FIG. 1) could be found from the equation:

$$P_{AOE} = P_{MCA} - \Delta_P \tag{5}$$

and $$\Delta_P = \frac{32 V_I \mu L}{D_I^2} = \frac{32 \cdot 0.24 \cdot 0.004 \cdot 0.012}{0.001^2} = 389\,Pa = 2.8\,mmHg. \tag{6}$$

It follows from equation (6) that the value of $\Delta_P$ is small compared to the measured value of the intracranial pressure $P_{IC}$ and could be neglected or compensated approximately as a measurement error.

5. Balance of pressures. The balances of pressures in internal point of measurement could be expressed as follows:

$$P_{ATM} + P_{IC} + P_{AWI} = P_{MCA} \tag{7}$$

where $P_{IC}$ is the intracranial pressure, $P_{ATM}$ is the atmospheric pressure, and $P_{AWI}$ is the pressure of the arterial wall.

The balance of pressure in the external point of measurement could be expressed as follows:

$$P_{ATM} + P_E + P_{AWE} = P_{AOE} \tag{8}$$

where $P_E$ is the additional external pressure added to the tissue surrounding the eyeball so that the external diameter $D_E$ of the OA is decreased until there is an equality with the internal diameter $D_I$, and $P_{AWE}$ is the pressure of the external optic artery arterial wall.

It is possible to formulate the equation of the pressure balance between internal and external points of measurement using the equation (5):

$$P_{ATM} + P_E + P_{AWE} = P_{ATM} + P_{IC} + P_{AWI} - \Delta_P \tag{9}$$

By this method only the values $P_E$, $V_E$ and $V_I$ are measured. If the value of external additional pressure $P_E$ is chosen so that $V_E = V_I$ that means that $D_E = D_I$. This is the result when a pressure balance is achieved. Then, $P_{AWI} = P_{AWE}$ and the final equation of pressure's balance could be expressed as:

$$P_{IC} = P_E + \Delta_P, \text{ if } V_E = V_I \tag{10}$$

It follows from equation (10) that the intracranial pressure $P_{IC}$ is approximately equal to $P_E$ if it is possible to neglect $\Delta_P$ and $P_{IC} = P_E$, if $\Delta_P$ is as small as calculated using equation (6) and either compensated for or tolerated as a measurement error.

With an apparatus in accordance with the invention I can measure the pressure inside a person's head without requiring direct measurements of intracranial pressure, arterial blood pressure $P_{MCA}$, hydrodynamic resistance of the OA eye branches or other individual parameters of patients, or require auto-regulation processes,. Only the value of $\Delta_P$ depends on $P_{MCA}$, $V_I$ and on other individual parameters. However, in most practical cases, the value of $\Delta_P$ can be ignored because it is not necessary, in clinical practices, to measure $P_{IC}$ with an absolute measurement error of less than +/−3 mmHg.

Figure 2:
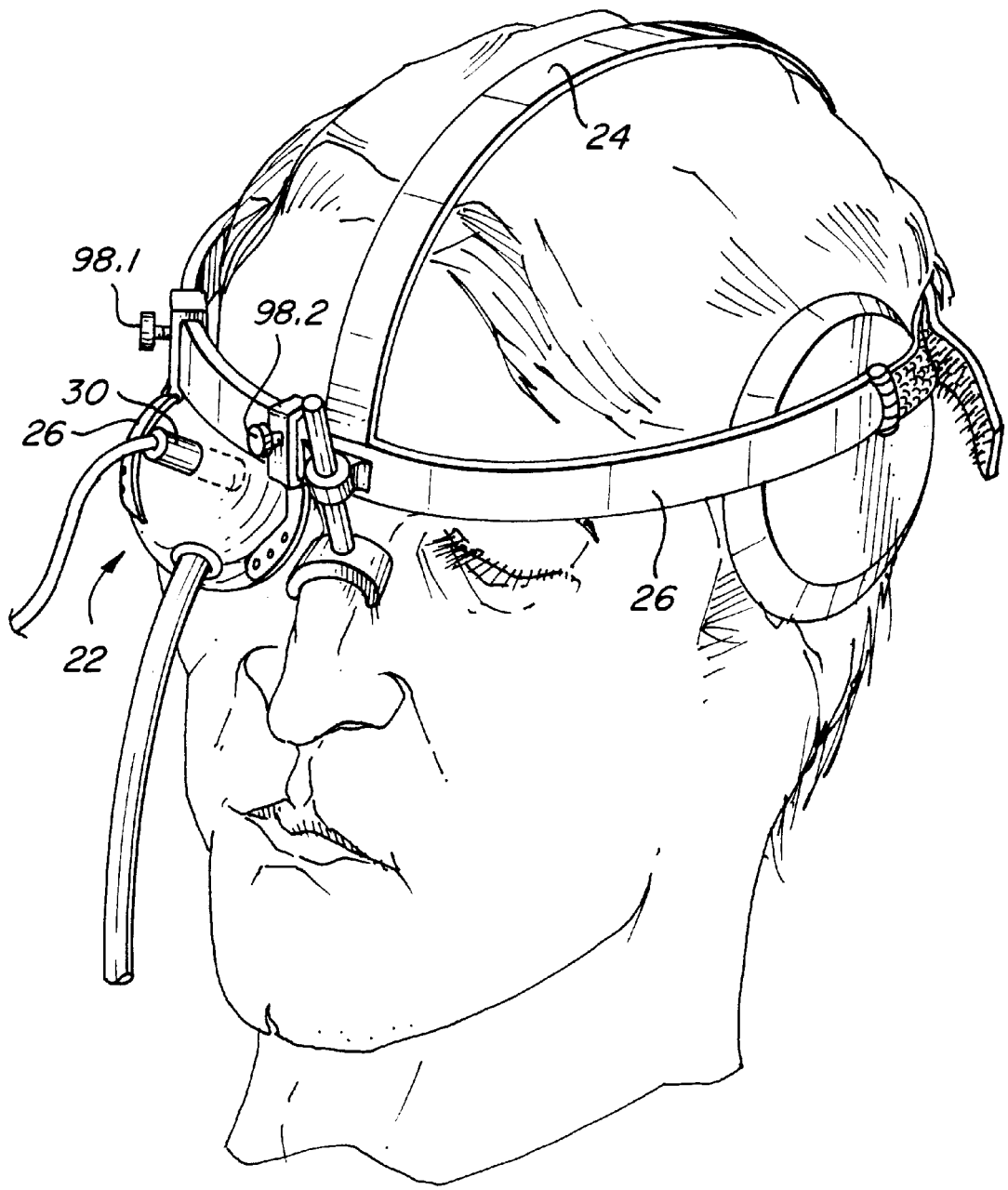
FIG. 2 is a perspective view of the mounting of an apparatus in accordance with the invention to a skull of a patient.

With reference to FIGS. 1 and 2 an apparatus 20 is shown to practice the measurement of the intracranial pressure as described above. The apparatus is mountable to the head of a person so that an eye engaging inflatable device 22 can apply a slight pressure against the eye lid 23. Suitable braces and positioning bands 24, 26 are used to hold the device 22 in place. The device 22 is formed of a suitable soft material such as rubber to form an inflatable chamber 28. Chamber 28 is approximately annular in shape so as to enable an ultrasonic transducer 30 to be mounted against an inner flexible membrane 32 and enable a pressurization of the chamber by a pump 34.

The inner membrane conforms to the shape of the eye 35 as illustrated and in such manner enable the pressure from the inflation of chamber 28 to provide a slight pressurization of the tissues surrounding the eye and thus the eye socket. This results in a pressurization of the optic artery 36, which originates from inside the cranium 40 and passes through the optic nerve channel 42 to the eye 35.

The ultrasonic transducer 30 has a central axis 44, which can be aligned by adjusting the position of the transducer inside its mounting to device 22. This alignment allows one to adjust the angle of axis 44 so as to direct its ultrasonic acoustic pulses at both interior and exterior portions 46, 48 of the optic artery 36 at the same angle. With such alignment Doppler measurements of the blood flow in these different portions 46, 48 can be made without the introduction of errors from the use of different angles of axis 44 with respect to portions 46 and 48. Hence, a reliable measurement of the intracranium pressure, $P_{IC}$ can be obtained.

The ultrasonic transducer 30 has its input line 50 coupled to an acoustic pulse transmitter 52. The transducer 30 also acts as a sonic receiver so that its input line 50 is connected to a gate 54. A gate input 56 is connected to the transmitter 52 to protect a receiver 58 from the high transmitter output pulses during pulsing of the transducer 30. The receiver 58 produces an output signal on line 60 representative of the acoustic echoes from the blood flow in the optic artery OA and caused by the ultrasonic pulses from the transmitter 52.

A depth control network 62 is provided to enable the apparatus 20 to select that portion of received echoes representative of either the internal or external, cranium, optic artery, blood velocities. The network 62 produces an internal selection signal on line 64 and an external selection signal on line 66. The internal selection signal is applied to an AND gate 67 to enable the echoes related to the blood flow inside the cranium to be selected for further processing. Similarly, the external signal is applied to an AND gate 68 to select the echoes related to the blood flow in the optic artery external of the cranium. The network 62 operates as a range gating system with which acoustic returns of different depths can be selected and analyzed for their Doppler frequency shift relative to the transmitter frequency $f_c$.

The internal and external selection signals are generated in sequence in a manner as is well known by a control 70 activated after each transmitter pulse by the signal on line 56. The outputs from AND gates 67, 68 are coupled through an OR gate 72 to a sampler frequency counter 74. This samples the received echo signals and produces sample signals, such as the signal frequency, $f_I$, in the pulse representative of blood velocity inside the cranium, the signal frequency, $f_E$, inside the echo pulse from the optic artery external of the cranium, and the frequency, $f_C$, in the transmitted pulse. The sampled frequency signals are stored at 76 in a suitable memory and at 78 the shifts in the frequencies from the frequency of the transmitted pulse, such as $f_c - f_I$ and $f_c - f_E$, are determined. A suitable microprocessor can be used to implement these functions.

Figure 5:
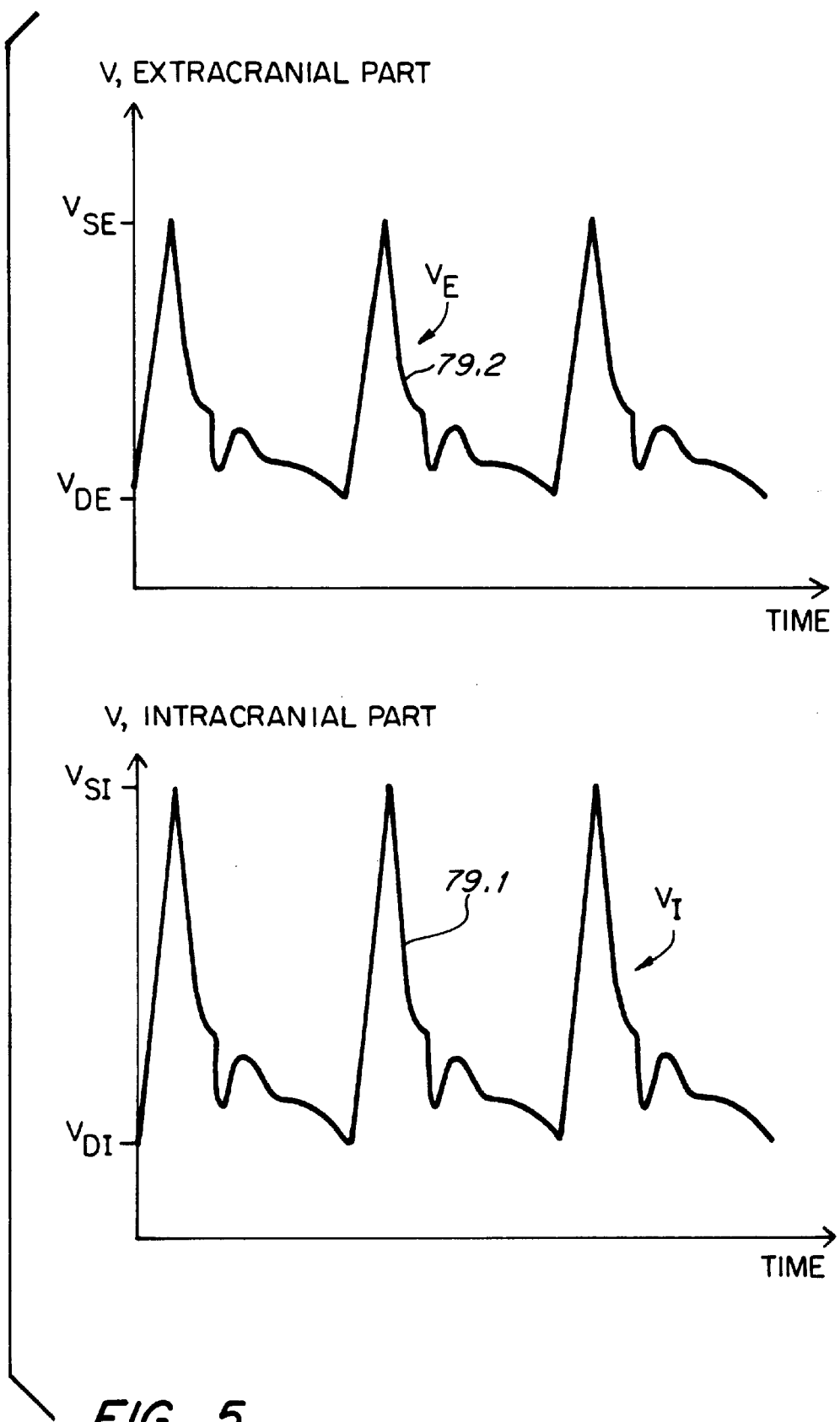
FIG. 5 are plots as a function of time of the blood velocity, V, pulsations in the internal and external parts of the optic artery.

The frequency shifts can be determined for each transmitter pulse and resulting echo. Each frequency shift is representative of the blood velocity in the optic artery and the values can be so stored to provide an indication of the internal blood velocity, $V_I$, and external blood velocity, $V_E$, at 78. These blood velocity signals can be displayed in a manner as shown in FIG. 5 with curves 79.1 and 79.2 or be superimposed as illustrated at 79.3 in FIG. 3 to more clearly show their relative levels or their difference, $\Delta V$, determined at 80. Note that the activation rate of the transmitter 52 is set sufficiently high so as to be able to determine the contours of the velocity curves 79. The velocity difference value $\Delta V$ can then be displayed and the display used to determine the intracranial pressure.

The difference values $\Delta V$ are used to determine the intracranial pressure $P_{IC}$. This is done by increasing the pressure inside the inflatable device 22 to a level where the difference values $\Delta V$ drop below a minimum level, $\Delta V_{min}$. This then becomes a resolution of the $V_I$ and $V_E$ measurements. The $P_{IC}$ measurement can be made by manually increasing the pressure inside the device 22 until the visual indications of the measured blood velocity signals $V_I$ and $V_E$, or the frequency shifts, appear the same or with an automatic control such as 82.

Alternatively an automatic control can be implemented, for example, by first testing at 84 whether the value of $\Delta V$ is below a minimum value such as $\Delta V_{min}$. If not, then at 86 a value for the pump pressure is incremented and its value applied to pump 34 to cause it to increase the pressure inside the inflatable device 22. A pressure transducer 90 senses the pressure inside the chamber 28 and produces a pressure signal, $P_m$, indicative thereof.

When the test at 84 shows positive, the value $P_m$ is stored at 92 as an indication of the internal cranium pressure, $P_{IC}$. This can be displayed at 94 and suitably recorded.

In the operation of apparatus 20 it desirable that an initial alignment mode be undertaken to assure that the transmitter pulses from the transducer 30 are properly directed at both the internal and external portions 46 and 48 of the optic artery 36. This involves adjustments in the angle φ between the axis 44 of the ultrasonic transducer 30 and the alignment axis 96 of the optic artery passage 42. Such adjustment can be done with the alignment screws 98.1 and 98.2 or with such other suitable frame affixed between the band 26 and the transducer 30 in FIG. 1.

Figure 4:
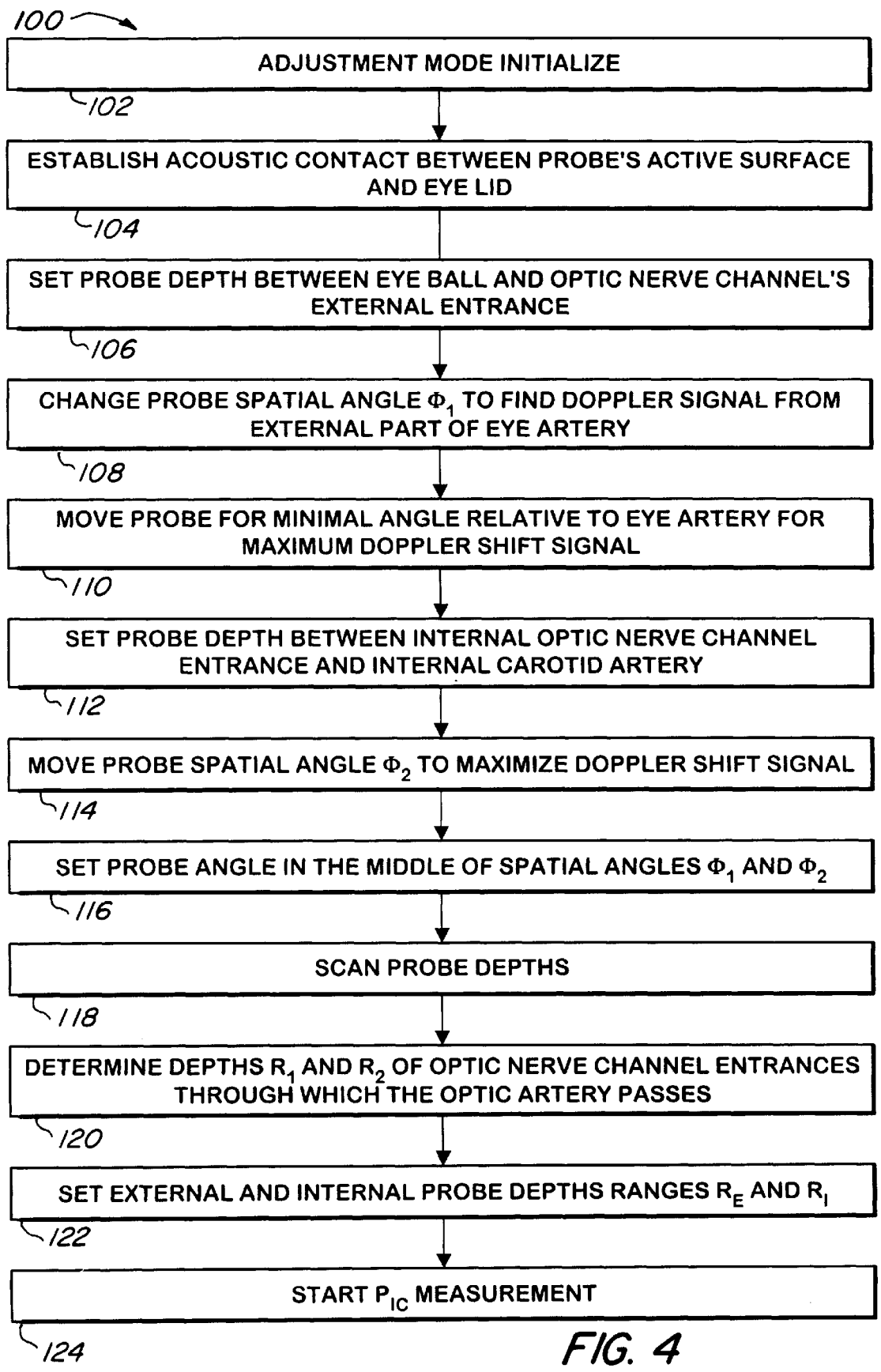
FIG. 4 is a flow chart for use in the apparatus of FIG. 1.

With reference to FIG. 4 a routine 100 for making such alignment is illustrated. Thus at 102 the apparatus 20 is initialized and at 104 operative contact between the acoustic transmitter 30 and the eye cavity is established by observing return echoes on a display. At 106 the depth of the operative probe depth $R_E$, see FIG. 1, is entered by the probe depth control block 70 ( See FIG. 1). Typical initial values of $R_E$ are approximately between 40 mm and 50 mm.

At 108 the spatial angle φ of the transducer axis 44 is changed to find the velocity signal associated with the external optic artery portion 48. This is found by observing the shape of the blood velocity pulsation curve of the extracranial part 48 of the optic artery 44, (see FIG. 5). The spatial angle, $\phi_1$, which yields the maximum Doppler signal level, is selected at 110 and noted.

At 112, the initial value of the internal probe depth $R_I$ is entered by the control block 70. The typical values of $R_I$ are approximately between 52 mm and 65 mm.

At 114 the spatial angle $\phi_2$ is determined for the alignment of the transducer 30 yielding the maximum Doppler signal pulsation from the internal portion 46 of the optic artery 36. The operating orientation of the transducer 30 is the selected at 116 by aligning the axis 44 of the transducer 30 along the middle between the angles $\phi_1$ and $\phi_2$.

Then at 118 the probe depth control 70 is actuated so that the blood velocities, within the internal and external optic artery portions 46, 48, are sequentially measured. The depths of external and internal optic nerve channel's entrances are determined by increasing $R_E$ from the values between those selected at 106 and the values selected at 112 while observing the blood velocity pulsation of FIG. 5. The blood velocity pulses have smaller amplitudes inside the optic nerve channel.

Then at step 120 the depths $R_1$ and $R_2$ of respectively the external and internal optic nerve channel entrances are determined. This is done by observing a decrease in the amplitudes of the blood velocity pulses, as shown in FIG. 5, and typical for measurements made inside the optic nerve channel in comparison with the amplitudes of blood velocity pulses from outside the optic nerve channel.

After that at step 122 the final value of $R_E$ and $R_I$ are set using the criteria $R_E < R_1$ and $R_I > R_2$.

Once the position of the ultrasonic transducer is determined and set a measurement of the internal and external blood velocities can be made as described above. A determination of the intracranial pressure $P_{IC}$ is obtained when the velocity measurements are the same.

Figure 3:
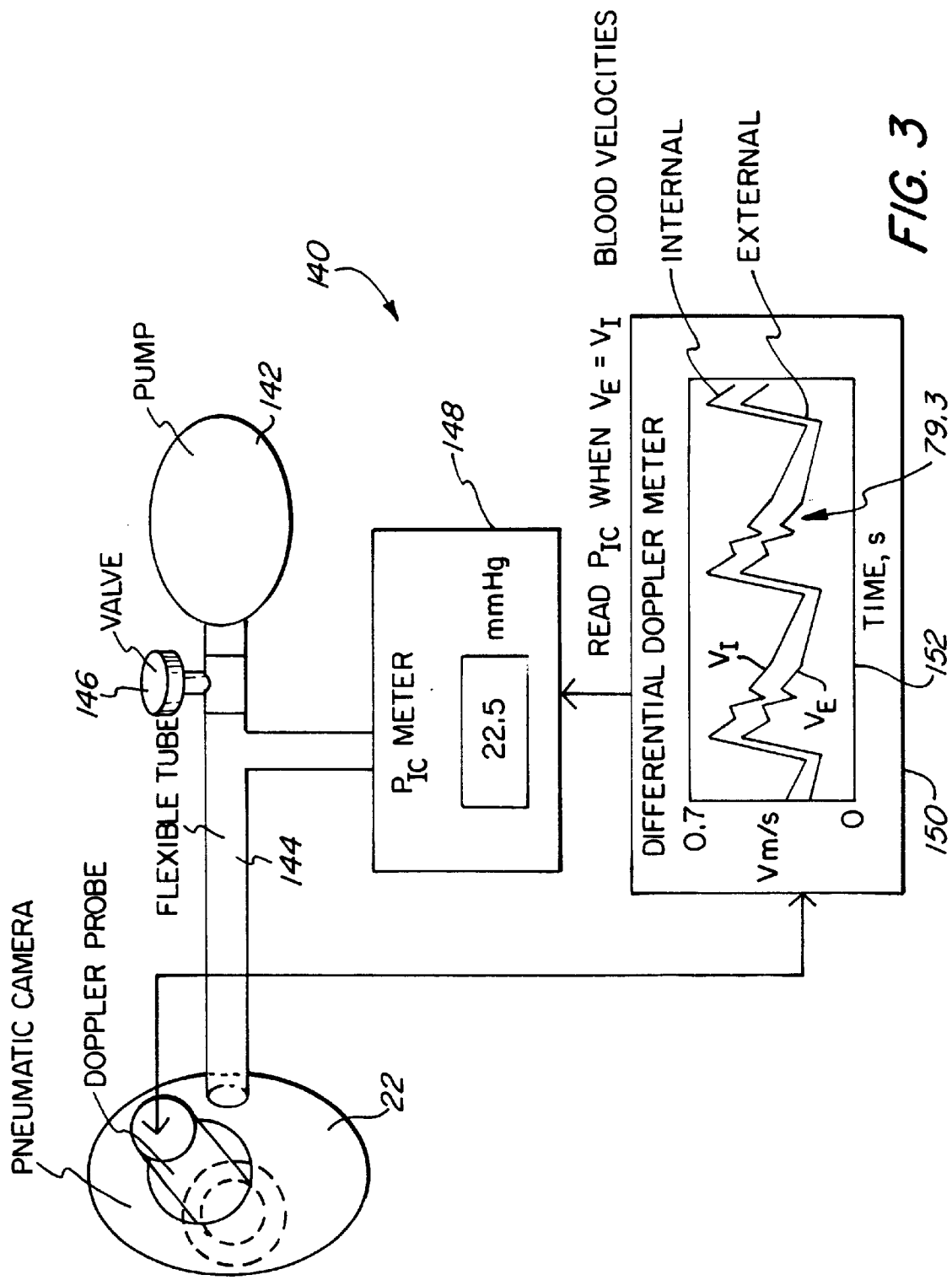
FIG. 3 is a simplified schematic and block diagram for illustrating the invention.

FIG. 3 illustrates a simplified system 140 for determining the internal cranium pressure. The system uses an inflatable device 22 as illustrated and described with reference to FIG. 1 and to which a manually activated pump 142, such as found with stethoscopes, is used. The pump 142 is connected to a flexible tube 144 through a valve 146 to inflate device 22. A pressure indicator 148 is coupled to the tube 144 to provide an indication of the pressure either in a visual or electronic form or both. An ultrasonic transducer 30 is activated by a control and Doppler meter 150 having a display 152.

When the values of the internal and external blood velocities appear to be the same, as can be observed from monitoring the display 152, a signal can be manually sent to the pressure meter 148 to store the pressure indication as a measurement of the intracranial pressure $P_{IC}$.

Having thus described illustrative apparatuses and techniques for determining the intracranium pressure in accordance with the invention, variations may occur to one skilled in the art. The embodiments described herein and other equivalent structures thereof can be contemplated by one skilled in the art and ought to be considered a part of the invention. For example, the particular circuitry shown in FIG. 1 can be done with other devices and logic circuits and in analog form as are well known by one skilled in the art. The invention should, therefore, be construed, in accordance as shown and described herein and in this paragraph as well as claimed in the following claims.

What is claimed is:

1. An apparatus for obtaining an indication of the intracranial pressure of a living body, comprising:

means for generating internal velocity and external velocity signals respectively representative of measured intracranial and external-cranium velocities of the blood flow in an optic artery extending from inside the cranium into an eye of the body;

means for applying an external pressure against the eye whose optic artery blood flow is measured; and means for identifying the intracranial pressure as that external pressure which causes the internal velocity and external velocity signals to represent the same blood flow velocity.

2. The apparatus as claimed in claim 1 wherein said generating means comprises:

means for directing ultrasonic pulses containing a reference acoustic frequency at said optic artery in a direction so as to cause and then detect acoustic reflections whose frequencies are altered by blood flows through the optic artery;

means responsive to said reflections for extracting first reflections containing frequencies altered by blood flow of the optic artery inside the cranium and second reflections containing frequencies altered by blood flow of the optic artery external of the cranium;

means for deriving deviations of frequencies in first reflections from the first reference frequency as indicative of the velocity of the blood flow velocity inside the cranium; and means for deriving deviations of frequencies in second reflections from the first reference frequency as indicative of the velocity of the blood flow velocity external of the cranium.

3. The apparatus as claimed in claim 1 wherein said identifying means comprises:

means for visually indicating said internal and external velocity signals.

4. The apparatus as claimed in claim 1 wherein said identifying means comprises:

means for comparing said internal and external velocity signals and produce a difference signal indicative thereof; and means responsive to said difference signal for varying the external pressure applying means until said internal and external velocity signals represent intracranial and external-cranium blood flow velocities which are substantially the same.

5. An apparatus for obtaining an indication of the blood flow inside an optic artery extending from inside the cranium of a body into an eye of the body, comprising:

means for applying an external pressure against the eye whose optic artery is being investigated; said pressure applying means including means for directing ultrasonic pulses of a predetermined frequency at intracranial and external-cranium portions of said optic artery and generating return signals from said optic artery; and means responsive to said return signals for extracting internal and external velocity signals respectively indicative of the velocity of the blood flow inside intracranial and external-cranium portions of the optic artery.

6. The apparatus as claimed in claim 5 wherein said means for extracting said velocity signals includes means for determining the internal and external ends of the optic nerve channel for the optic artery;

range gating means for internal selecting return signals representative of acoustic echoes from the blood flow in said optic artery inside the cranium and before the determined optic nerve channel and external return signals representative of acoustic echoes from the blood flow in said optic artery in said eye and outside of said optic nerve channel;

means for determining the Doppler frequency shift in said selected internal and external return signals relative to the frequency in said transmitter pulses and store signal values indicative of the velocities of the intracranium and extracranium blood flow in said optic artery.

7. The apparatus as claimed in claim 6 and further including means for increasing the external pressure until a difference between said velocity signal values drops below a predetermined minimum and storing a signal indicative of said external pressure when the difference drops below said minimum value.

8. The apparatus as claimed in claim 7 and means for displaying said stored external pressure.

9. A method for obtaining an indication of the intracranial pressure of a living body, comprising the steps of:

generating internal velocity and external velocity signals respectively representative of measured intracranial and external-cranium velocities of the blood flow in an optic artery extending from inside the cranium into an eye of the body;

applying an external pressure against the eye whose optic artery blood flow is measured; and identifying the intracranial pressure as that external pressure which causes the internal velocity and external velocity signals to represent the same blood flow velocity.

10. The method of claim 9 and further comprising the step of: displaying the identified intracranial pressure.

11. The method as claimed in claim 9 and wherein said identifying step comprises the steps of:

comparing the measured internal and external velocity signals to produce an error velocity signal indicative thereof;

applying the error signal to cause a change in the external pressure applied against the eye so as t drive the error signal to a minimum value; and storing the external pressure as the intracranial pressure when the internal and external velocity signals are substantially the same.

12. The method as claimed in claim 10 wherein said step of generating internal and external velocity signals comprises:

generating ultrasonic pulses into the eye and towards the optic artery so as to intersect both internal and external portions thereof; and detecting echoes from said optic artery portions and deriving Doppler variations therefrom as said internal and external velocity signals.

* * * * *